(12) United States Patent
Koike et al.

(10) Patent No.: US 6,571,114 B1
(45) Date of Patent: May 27, 2003

(54) MEDICAL MEASUREMENT APPARATUS

(75) Inventors: Kazuo Koike, Tokyo (JP); Yasufumi Hisasue, Tokyo (JP); Toshihiro Noguchi, Yokohama (JP); Shoji Yokota, Yokohama (JP)

(73) Assignee: Koike Medical Co., Ltd., Tokyo (JP)

( * ) Notice: Subject to any disclaimer, the term of this patent is extended or adjusted under 35 U.S.C. 154(b) by 0 days.

(21) Appl. No.: 09/763,611

(22) PCT Filed: Nov. 2, 1999

(86) PCT No.: PCT/JP99/06103

§ 371 (c)(1),
(2), (4) Date: Jun. 4, 2001

(87) PCT Pub. No.: WO01/03582

PCT Pub. Date: Jan. 18, 2001

(51) Int. Cl.[7] .................. A61B 5/145; A61B 5/0245
(52) U.S. Cl. ........................ 600/323; 600/476
(58) Field of Search ................. 600/322, 323, 600/324, 326, 476, 480, 479

(56) References Cited

U.S. PATENT DOCUMENTS

| | | | |
|---|---|---|---|
| 4,844,084 A | * | 7/1989 | Yamasawa ............... 600/480 |
| 5,218,966 A | * | 6/1993 | Yamasawa ............... 600/480 |
| 5,438,201 A | * | 8/1995 | Rosenthal et al. ......... 600/310 |
| 5,452,717 A | * | 9/1995 | Branigan et al. .......... 600/323 |
| 5,490,523 A | * | 2/1996 | Isaacson et al. .......... 600/323 |
| 5,807,266 A | * | 9/1998 | Itonaga et al. ............ 600/479 |
| 5,830,135 A | * | 11/1998 | Bosque et al. ............ 600/323 |
| 5,891,022 A | * | 4/1999 | Pologe .................... 600/310 |
| 6,006,120 A | * | 12/1999 | Levin ...................... 600/323 |
| 6,151,516 A | * | 11/2000 | Kiani-Azarbayjany et al. .. 600/323 |

FOREIGN PATENT DOCUMENTS

JP   2-17031   * 1/1990

* cited by examiner

*Primary Examiner*—John Rivell
(74) *Attorney, Agent, or Firm*—Townsend & Banta

(57) ABSTRACT

This invention regarding the medical measurement apparatus includes an apparatus body capable of being held with a thumb and at least one of the subject testing-fingers, that is, the forefinger, the middle finger, the third finger, the fourth finger; a sensor slot bearing within a sensor in which the sensor slot is open at the side of the apparatus body capable of inserting the testing finger; a switch of the sensor in which the switch is controlled by the thumb and disposed at a prescribed position of the apparatus body; and a display device for indicating the result measured by the sensor in which the display device is arranged at the front surface of the apparatus body.

6 Claims, 4 Drawing Sheets

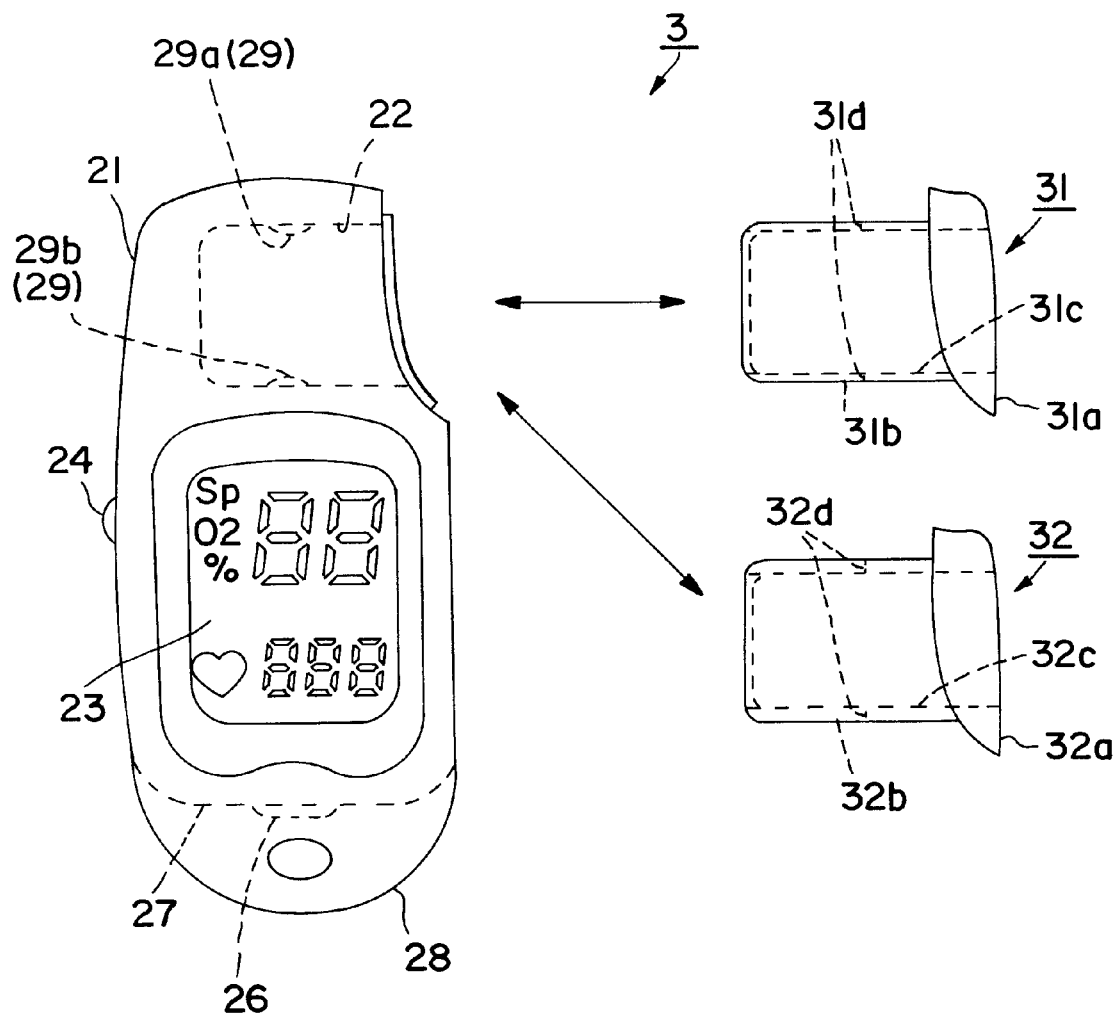
F I G. 5

MEDICAL MEASUREMENT APPARATUS

BACKGROUND OF THE INVENTION

1. Field of the Invention

This invention relates to a united bodied apparatus comprised of a display component and a sensor for measuring the arterial oxygen saturation value, the pulse rate and the like by applying a finger to the sensor and, more particularly, relates to an apparatus in which the apparatus body could be held with a thumb and a testing finger subject to measurement by the sensor and, thus could be single-handedly operated.

2. Description of Related Art

Conventionally, the commonly used medical measurement apparatus for detecting the arterial oxygen saturation value or the pulse rate was a measurement apparatus having a measurement apparatus body with a display unit, a probe bearing a sensor for measuring a subject testing finger in which the measurement apparatus body and the probe were connected by a cord. However, due to the recent size reduction of the element comprising the measurement circuit, an independent measurement apparatus in which the sensor and the display unit constitute a united body has been developed, for example, as disclosed in Japan Publication No.10-502268.

The foregoing measurement apparatus has a structure in which the primary housing and the secondary housing are urged with a spring and detachably united and thus the subject testing finger could be held between the housings. In respect of a sensor comprised of a pair of a light emitting body and a light receiving body, the light emitting body is attached to the primary housing and the light receiving body is attached to the secondary housing; accordingly, the light transmits through the subject testing finger, and by measuring the received light the arterial oxygen saturation value or the pulse rate could be measured. The measured result is then indicated on the display unit attached to the primary housing.

Nevertheless, in respect of the conventional measurement apparatus with the so-called clip type structure, during the attachment to the subject testing finger, in order to insert the subject testing finger between the primary housing and the secondary housing, a task in which a prescribed portion had to be pressed with the other hand was necessary. This task raised a problem of making the use difficult in a state where for some reason one of the hand cannot be used.

In addition, in respect of the conventional clip type structure, the separated structure in which the primary housing and the secondary housing are disjunctive raised other problems as the unavoidable increasing of the apparatus capacity and the limiting of size reduction e.g., due to the relation with the size of the display unit.

Furthermore, with the conventional clip type structure, since the attachment to the subject testing finger relies on the urging of the spring, depending on the thickness of the finger or the preset urging force of the spring, a sense of constriction might be felt and would raise a problem of obstructing the performance of a comfortable measuring procedure.

Therefore, the object of this invention is to provide a medical measurement apparatus in which the apparatus body could be held with a subject testing finger and a thumb; wherein the medical measurement apparatus could be single-handedly used by making a switch of the measurement apparatus into a structure capable of being operated with a thumb; wherein the entire apparatus could be made more compact; and furthermore, without arousing an uncomfortable constricting feeling upon the subject testing finger.

SUMMARY OF THE INVENTION

In order to accomplish the foregoing object, this invention regarding the medical measurement apparatus includes an apparatus body capable of being held with a thumb and at least one of the subject testing-fingers, that is, the forefinger, the middle finger, the third finger, the fourth finger; a sensor slot bearing within a sensor in which the sensor slot is open at the side of the apparatus body capable of inserting the testing finger; a switch of the sensor in which the switch is controlled by the thumb and disposed at a prescribed position of the apparatus body; and a display device for indicating the result measured by the sensor in which the display device is arranged at the front surface of the apparatus body.

In addition, the sensor disposed inside the sensor slot could be a sensor for measuring the arterial oxygen saturation value. In respect of the apparatus body, by forming the portion where the switch is arranged into a grooved state extending along the longitudinal direction of the thumb, the thumb for controlling the switch could be firmly secured.

Furthermore, by making a sensor slot member comprising the sensor slot into a structure capable of attaching to and detaching from the apparatus body, the sensor slot could be detached from the apparatus body and washed; accordingly, a more hygienic medical measurement apparatus could be provided. By preparing a variety of sensor slot members having different inner-diameters and thus making the sensor slot members selectable, a sensor slot suited for the size of the user's finger could be provided; accordingly, a more comfortable medical measurement apparatus could be provided.

In addition, by arranging a sound device to inform whenever the sensor detects a measurement result exceeding a predetermined numerical limit, the user could instantly know the bodily changes and would become useful in controlling the user's physical condition.

BRIEF DESCRIPTION OF THE DRAWINGS

The above and other objects and features of the invention are apparent to those skilled in the art from the following preferred embodiments thereof when considered in conjunction with the accompanied drawings, in which:

FIG. 5 is a front view of the medical measurement apparatus according to the third embodiment of the invention

DESCRIPTION OF THE PREFERRED EMBODIMENTS

First Embodiment

Figure 1A:
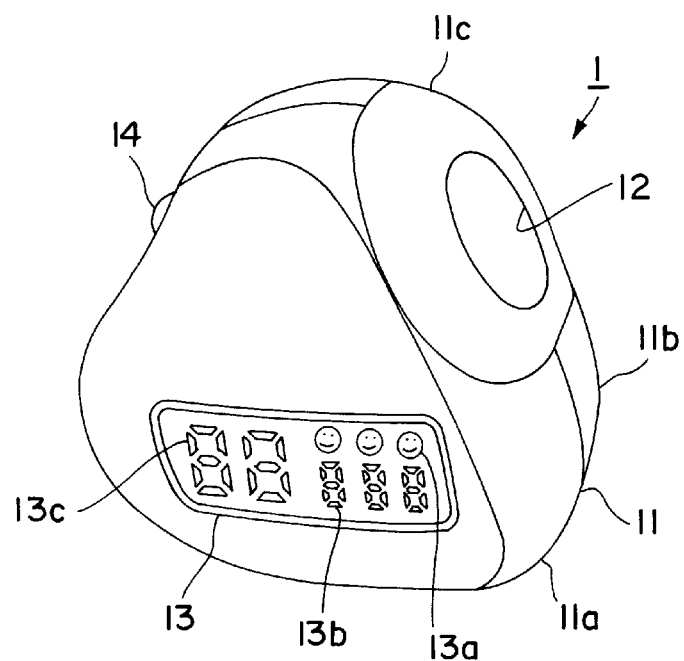
FIGS. 1(*a*) and (*b*) are both the perspective views of a medical measurement apparatus according to the first embodiment of the invention.
Figure 1B:
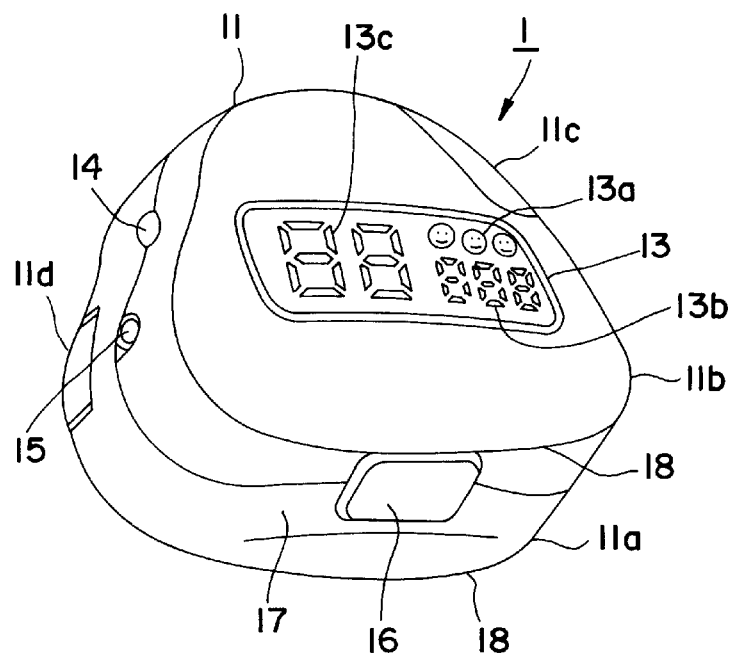
Figure 2:
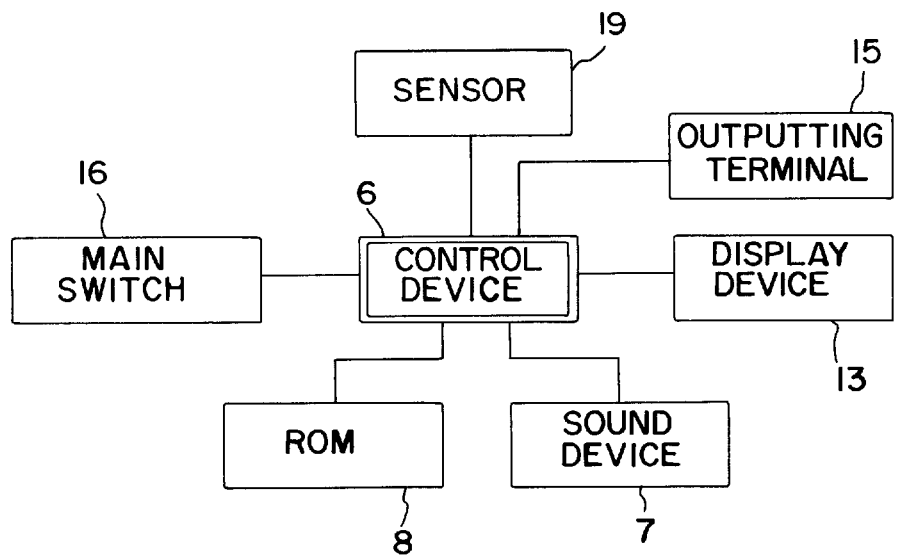
FIG. 2 is a block diagram of the control circuit for the medical measurement apparatus according to the first embodiment of the invention.
Figure 3:
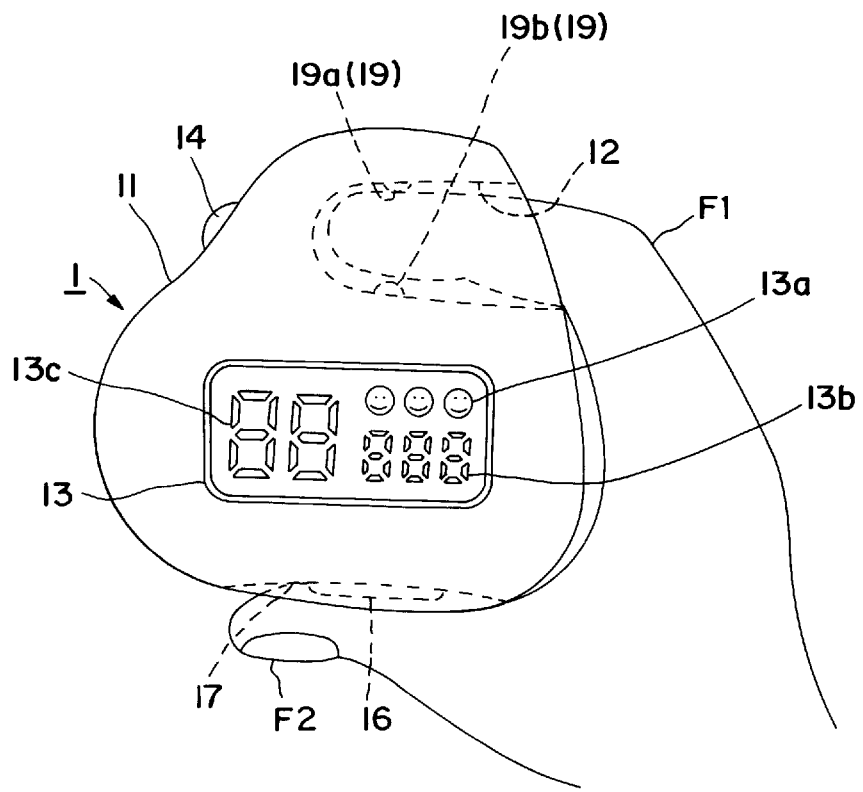
FIG. 3 is a descriptive view showing the used state of the medical measurement apparatus according to the first embodiment of the invention.

A first embodiment of the medical measurement apparatus (hereinafter referred to as measurement apparatus) will hereinafter be described with reference to the following drawings. According to the first embodiment of the invention, both (*a*) and (*b*) of FIG. 1 are the perspective views of the measurement apparatus, FIG. 2 is a block diagram of the control circuit for the measurement apparatus, FIG. 3 is a descriptive view showing the used state of the measurement apparatus. The measurement apparatus of this embodiment is a portable measurement apparatus for measuring the arterial oxygen saturation value and the pulse rate in which the apparatus could be used at hospitals or for domestic nursing.

As shown in both (*a*) and (*b*) of FIG. 1, the measurement apparatus 1 is largely comprised of an apparatus body 11, a sensor slot 12 for inserting the subject testing finger, a display device 13 for indicating the measurement result, and a main switch 16 for activating the measurement apparatus 1.

Having the front shaped as a heart, the main body 11 is comprised of a primary casing 11*a* of the front side, a secondary casing 11*b* of the rear side, and a sensor slot component 11*c*, and furthermore, as shown in the block diagram of FIG. 2, a control unit 6, a sound device 7 amd a ROM 8 are built inside.

Attached at the center of the primary casing 11*a* is a display device 13 serving as a liquid crystal display unit. In respect of the secondary casing 11*b*, formed at a portion of the secondary casing 11*b* is a lid for the battery containment portion 11*d* in which the battery containment portion 11*d* would serve as the activating power source for the measurement device 1. In respect of the sensor slot component 11*c*, a sensor slot 12 bearing a cylindrical slot is formed and is assembled with the primary casing 11*a* and the secondary casing 11*b* in a sandwiched manner forming a united body.

The sensor slot 12 has an opening with a diameter of substantially 2 centimeters capable of inserting the subject testing finger, that is, the forefinger F1; thus, inside the sensor slot 12 is an optical sensor 19(see FIG. 3). The sensor 19 is comprised by a pair of a light emitting member 19*a* built at the upper portion of the sensor slot 12 and a light receiving member 19*b* built at the lower portion of the sensor slot 12 and, by the transmission of light upon the subject testing finger placed between the light emitting member 19*a* and the light receiving member 19*b*, the light receiving member 19*b* captures the changes of light and measures the arterial oxygen saturation degree and the pulse rate.

In means to prevent the external diffused light noise, the sensor slot component 11*c* constituting the sensor slot 12 could be formed with materials of low light transmittancy such as polycarbonite (PC) resin included with a glass filler, or on the other hand, the sensor slot component 11*c* constituting the sensor slot 12 could be coated with a paint of an effective light-shielding color or a paint of a thick film.

The display device 13 serving as a crystal display panel is comprised of a pulse level display column with face marks 13*a*, a three digit pulse rate display column 13*b* operating the main switch 16 or the backlight switch 14, and also makes a sound synchronizing with the timing of the pulse rate.

Furthermore, the ROM 8 memorizes the control program of the control circuit and accordingly, the control device 6 controls the sensor 19, the display device 13, the sound device 7.

Next, the operating procedure regarding this embodiment of the measurement will hereinafter be described-with reference to FIG. 3. First, the subject testing finger, that is, the forefinger F1 of the right hand is inserted into the sensor slot 12 arranged at the upper portion of the apparatus body 11, and then, by placing the thumb F2 of the right hand on the main switch 16 of the lower portion of the apparatus body 11, the measurement apparatus 1 could be held between the forefinger F1 and the thumb F2.

In addition, when the forefinger could not be used as a subject testing finger for some reason, any one of the middle finger, the third finger, the fourth finger could be used instead.

Furthermore, in a state where the forefinger F1 is sufficiently inserted deep inside the sensor slot 12, in accordance with the pressing of the main switch 16 by the thumb F2, the sensor 19 is activated and the measuring of the pulse rate and the arterial oxygen saturation value would begin.

In thus state, the sensor 19 does not only measure the pulse rate but at the same time measures the pulse level (strength of the pulse) as well. In accordance with the strength of the pulse, the face marks are indicated at the pulse level display column 13*a* of the display device 13.

Furthermore, during the measuring process, the sound device 7 makes an intermittent sound synchronizing with timing of the pulse rate measured by the sensor 19; therefore, the user would not only recognize the pulse rate from the display of the display device 13 but could recognize the pulse rate from sound as well.

When the sensor 19 completes measuring for a prescribed time, the and a double-digit arterial oxygen saturation display column 13*c*. This display device 13 has a backlight function, and when necessary, the display device 13 could be illuminated for a prescribed period by the switch arranged at the side of the apparatus body 11.

The main switch 16 is arranged at the bottom surface of the apparatus body 11. This main switch 16 is a pressing type switch, and by turning the switch 16 on, the sensor 19 could be activated; then based on the measured information read by the sensor, the control unit (see FIG. 2) measures the pulse level, the pulse rate, ok the arterial oxygen saturation value and then the result is indicated on the display device 13.

The bottom portion of the apparatus body 11 where the main switch 16 is arranged has a shallow grooved surface 17 and formed on both sides are the guide members 18. Accordingly, when a thumb F2 (see FIG. 3) is applied to the main switch 16, the thumb F2 would fit along the grooved surface 17 in the longitudinal direction.

At the side of the apparatus body 11, an outputting terminal 15 for outputting information is arranged below the backlight switch 14. By connecting the information outputting terminal 15 to a computer or a printer, the measured information by the measurement apparatus 1 could be externally outputted and be made to use.

In addition, at the rear surface of the apparatus body 11 (not shown) a portion for attaching a strap is formed and by attaching a strap to thus portion, the medical measurement apparatus could be hung around the hand or the neck and be easily carried.

The control circuit of the measurement apparatus 1 will hereinafter be described with reference to FIG. 2. As shown in the said figure, in respect of the control circuit of the measurement apparatus 1, a control device 6 is positioned at the center in which the sensor 19, the display device 13, the outputting terminal 15, the sound device 7, the ROM 8 are connected to the control device 6 respectively.

The sound device 7 is a device, which makes a confirmatory sound when measurement result is displayed at the display device 13 via the calculating circuit of the control device, and the process is completed by the displaying of the pulse rate at the pulse rate display column 13b along with the displaying of the arterial oxygen saturation value at the arterial oxygen saturation value display column 13c. In addition, although thus display is programmed to be shown as long as the main switch 16 is pressed, the time of display could be specified to a predetermined length as well.

In addition, for use at night or for use in the dark, by pressing the backlight switch beforehand and performing the foregoing consecutive procedures, the measurement reading could be displayed in a state where the backlight is illuminated.

Furthermore, by connecting a cable to the outputting terminal 15, the measurement result of the measurement apparatus 1 could be outputted to an exterior computer. In addition, by consecutively storing the daily measurement result with the exterior computer, the results could be used as long term information for physical conditioning. By connecting the measurement apparatus 1 and an exterior printer via the outputting terminal 15, the measurement result could be outputted onto paper and stored as a record.

Furthermore, a control program could be assembled wherein the limit of the normal pulse rate and the normal arterial oxygen saturation value are memorized into ROM 8 beforehand, and thus the control device 6 would then compare the measurement result measured by the sensor 19 with the foregoing limit, and the sound device 7 would make a warning sound whenever the measurement reading exceeds thus limit.

As described above, in respect of the measurement apparatus 1 according to this embodiment, since the holding of the apparatus body 11 and the controlling could be accomplished with the subject testing finger and the thumb and could be single-handedly operated, thus apparatus is easy to use for the user and is highly convenient.

Figure 4A:
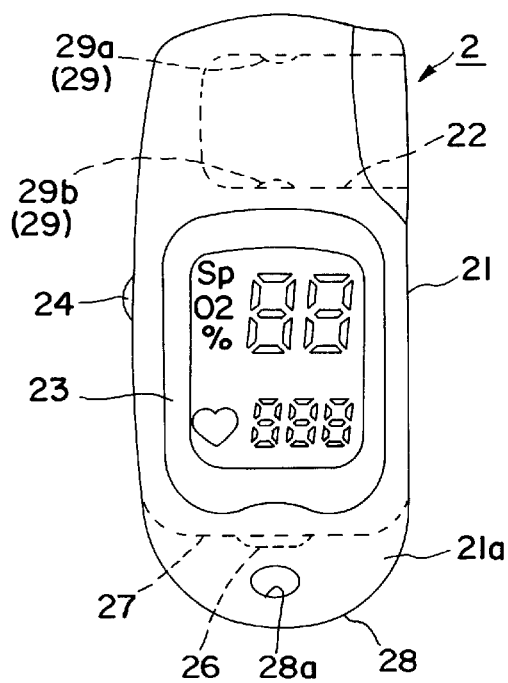
FIG. 4(*a*) is a front view of the medical measurement apparatus according to the second embodiment of the invention, and FIG. 4(*b*) is a side view showing the medical measurement apparatus according to the second embodiment of the invention.
Figure 4B:
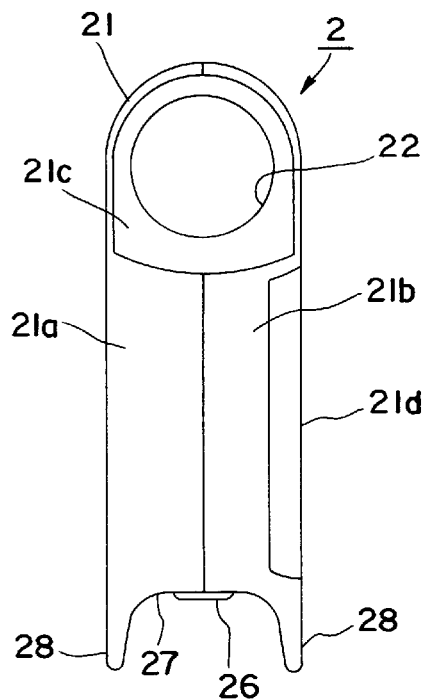

A second embodiment of this invention will hereinafter be described with reference to FIG. 4. This embodiment regarding a measurement apparatus 2 shown in the figure is an example showing the diversity of the measurement apparatus in which apparatus body 21 is formed with a rectangular front. FIG. 4(a) is a front view of the measurement apparatus, and FIG. 4(b) is a side view of the measurement apparatus.

As shown in FIGS. 4(a) and (b), the measurement apparatus 2 includes an apparatus body 21, a sensor slot 22 for inserting a subject testing finger, a display device 23 for displaying the measurement result, and a main switch 26. Furthermore, the apparatus body 21 is comprised of a primary casing 21a of the front surface, a secondary casing 21b of the rear surface, and a sensor slot component 21c; and same as the first embodiment, the control device 6, the sound device 7, the ROM 8 are provided inside.

Arranged at the bottom portion of the apparatus body 11, the main switch 26 is surrounded by a grooved surface in which the guide member 28 is formed on both sides. The guide member 28 is formed higher than that of the first embodiment and also a strap attachment slot 28a is formed at the guide member 28. Further, formed at the left side of the apparatus body 21 is a backlight switch 24, and though not illustrated, the outputting terminal for connecting to an exterior computer or a printer is arranged at the lower portion of the backlight switch 24.

In addition, since the operating procedure of the measurement apparatus 2 of this embodiment is the same as the first embodiment, thus description shall be omitted.

Furthermore, a third embodiment of this invention will hereinafter be described with reference to FIG. 5. Regarding a measurement apparatus 3 of this embodiment, the sensor slot members are structured in a manner capable of attaching to and detaching from the apparatus body 21, and further structured so that a plurality of sensor slot members 31,32 having sensor slots of different diameter could be prepared and selectively attached to the apparatus body.

In addition, since most portions of this embodiment such as the display device 23 and the main switch 26 bear the same structure as that of the second embodiment, the same numbers shall be assigned to the same corresponding portions and the description of the portions shall therefore be omitted.

Regarding the measurement apparatus 3 of this embodiment, the primary sensor slot component 31 and the secondary sensor slot component 32 are provided in a manner so that the sensor slots are selectable and thus capable of attaching to and detaching from the sensor slot 22 of the apparatus body 21. These two sensor slot components 31, 32 are members, which are molded into a united body with a synthetic resin and are respectively comprised of the openings 31a, 32a and the cylindrical portions 31b, 32b; further formed at the cylindrical portions 31b, 32b are the inner slots 31c, 32c. In addition, the slits corresponding to the sensor 31d, 32d are formed at the upper and lower portions of the cylindrical portions 31b, 32b respectively so that the sensor slot components 31, 32 would not contact the projecting sensor 29 inside the sensor slot 22 when the cylindrical portions 31b, 32b are inserted into the sensor slot 22.

The inner slot 31c of the primary sensor slot component 31 has a relatively large diameter (e.g. 20 mm), while on the other hand, the inner slot 32c of the secondary sensor slot component 32 has a relatively small diameter (e.g. 18 mm); accordingly, the user can select from either one of the sensor slot components which is most suited for his or her finger.

Furthermore, regarding the measurement apparatus 3 of this embodiment, by making the sensor slot components 31, 32 detachable, the portion which always makes contact with the subject testing finger of the user could be cleaned; accordingly, a highly hygienic apparatus could be provided.

By preparing a variety of sensor slot components 31, 32 in which the inner slots 31c, 32c have different inner diameters, in accordance with the size of the user's finger, the user can select the suitable sensor slot components 31, 32. Although the light entering from outside would obstruct the providing of a desired sensitivity during the activation of the sensor 29, by selecting the sensor slot component 31, 32 in accordance with the suitable size of the user's finger, the entering of the outer light would be restricted; consequently, the measuring with a high sensitivity could be performed.

In addition, although the foregoing measurement apparatus regarding the embodiments 1 to 3 showed the examples of a measurement apparatus with a sensor slot formed at the front-right surface for right hand use, the measurement apparatus could be formed having the sensor slot at the front-left surface for left hand use as well.

Furthermore, although thus measurement apparatus regarding the embodiments 1 to 3 is provided with the main switch arranged at the bottom surface of the apparatus body, thus arrangement is not mandatory; for example, a slot could be formed aligned with the sensor slot wherein the switch is arranged within thus slot.

Although the measurement apparatus of the foregoing embodiments showed the examples of an apparatus for measuring the pulse rate and the arterial saturation value, the apparatus could be used for measuring the blood pressure or for measuring other medical testing data as well. In thus occasion, the sensor should not be limited to an optic sensor mentioned above.

Consequently, as described above, with this invention regarding the medical measurement apparatus, since the apparatus body could be held by the subject testing Finger and the thumb and since the measurement apparatus could be operated with the thumb in thus state, a highly maneuverable medical measurement apparatus would be provided.

Furthermore, with this invention regarding the medical measurement apparatus, the subject testing finger would not have to be measured in a clipping manner as that of the conventional apparatus, and thus the conventional uncomfortable constricting feeling would not be aroused; accordingly a comfortable medical measurement apparatus would be provided.

In addition, with this invention regarding the medical measurement apparatus, since the display device is arranged at the center of the apparatus body held by the subject testing finger and the thumb, when the apparatus is casually held by the hand, the display device would be brought to a highly visible position facing the front of the user; accordingly, a medical measurement apparatus in which the user could easily a recognize the measurement result would be provided.

What is claimed is:

1. A medical measurement apparatus comprising:
   an apparatus body capable of being held with a thumb and at least one of the subject testing-fingers constituted of the forefinger, the middle finger, the third finger and the fourth finger;
   a sensor slot bearing within a light receiving element of a optical sensor at a lower portion of the sensor slot in which the sensor slot is open at a side of upper portion of the apparatus body capable of inserting the subject testing finger;
   a switch of the sensor in which the switch is controlled by the thumb and disposed at bottom surface of the apparatus body; and
   a display device for indicating the measurement result by the sensor in which the display device is arranged at a front surface of the apparatus body.

2. The medical measurement apparatus according to claim 1, wherein the sensor disposed inside the sensor slot is a sensor for measuring the arterial oxygen saturation value.

3. The medical measurement apparatus according to claim 1, in respect of the apparatus body, a portion in which the switch is arranged has a groove extending along the longitudinal direction of the thumb.

4. The medical measurement apparatus according to claim 1, wherein a sensor slot member forming the sensor slot bears a structure capable of attaching to and detaching from the apparatus body.

5. The medical measurement apparatus according to claim 4, wherein a variety of sensor slot members having different inner-diameters could be prepared and selectively attached to the medical measurement apparatus.

6. The medical measurement apparatus according to claim 1, further comprising a sound device for informing a situation in which the reading measured by the sensor exceeds a predetermined numerical limit.

* * * * *